United States Patent [19]
Crowely

[11] Patent Number: 5,855,555
[45] Date of Patent: Jan. 5, 1999

[54] MRI SYSTEM AND METHOD FOR IMAGING SKIN

[76] Inventor: Christopher W. Crowely, 5921 Scripps St., San Diego, Calif. 92122

[21] Appl. No.: 779,158

[22] Filed: Jan. 6, 1997

[51] Int. Cl.$^6$ .................................................. A61B 5/055
[52] U.S. Cl. ........................ 600/421; 600/422; 324/309; 324/318
[58] Field of Search .................................. 600/410, 421, 600/422; 324/307, 309, 318, 322; 335/296, 302, 304

[56] References Cited

U.S. PATENT DOCUMENTS

| | | |
|---|---|---|
| 4,093,912 | 6/1978 | Double et al. . |
| 4,122,386 | 10/1978 | Tomita et al. . |
| 4,254,778 | 3/1981 | Clow et al. . |
| 4,422,042 | 12/1983 | Sugimoto . |
| 4,521,733 | 6/1985 | Bottomley et al. . |
| 4,542,343 | 9/1985 | Brown . |
| 4,721,914 | 1/1988 | Fukushima et al. . |
| 4,818,966 | 4/1989 | Miyamoto et al. . |
| 4,870,363 | 9/1989 | Yassine et al. . |
| 5,003,276 | 3/1991 | Sarwinski et al. . |
| 5,134,374 | 7/1992 | Breneman et al. . |
| 5,304,930 | 4/1994 | Crowley et al. . |

OTHER PUBLICATIONS

*In Vivo MR Microscopy of the Human Skin*, Song et al., pp. 185–191, Magnetic Resonance In Medicine, vol. 37, No. 2, Feb. 1997.

*Nuclear Magnetic Resonance Microscopy with 4–μm Resolution: Theoretical Study and Experimental Results*, Z. H. Cho et al., Medical Physics, vol. 15, No. 6, Nov./Dec. 1988.

*Echo Projection Imaging—A Method to Obtain NMR Images Undistorted by Magnetic Field Inhomogeneities*, Peter Bendel, IEEE Transactions on Medical Imaging, vol. MI–4, No. 2, Jun. 1985.

*Primary Examiner*—Ruth S. Smith
*Attorney, Agent, or Firm*—Nydegger & Associates

[57] ABSTRACT

The present invention is an MRI system for imaging small superficial volumes, such as skin samples. Structurally, the present invention includes a permanent magnet formed to establish a channel. The permanent magnet establishes a static magnetic field within the channel having an imaging volume that is much smaller than the channel. The present invention also includes a probe having a tip. A gradient and radio frequency coil and a radio frequency sensing coil are mounted at the tip of the probe. Functionally, an object such as a human hand, is placed within the channel with the selected skin volume placed against the tip of the probe. Once so placed, atomic nuclei within the object become aligned with the static magnetic field. The gradient and radio frequency coils are then selectively enabled and disabled causing the atomic nuclei to alternately realign and relax. During relaxation, the atomic nuclei produce a characteristic signal which is sensed by the radio frequency sensing coil and assembled into a digital image of the object being imaged.

21 Claims, 1 Drawing Sheet

MRI SYSTEM AND METHOD FOR IMAGING SKIN

FIELD OF THE INVENTION

The present invention pertains generally to medical devices and procedures. More particularly, the present invention pertains to devices and methods for producing images of small superficial tissue volumes. The present invention is particularly, but not exclusively useful, as a device for gathering a magnetic resonance image of the skin.

BACKGROUND OF THE INVENTION

The use of nuclear magnetic resonance phenomena for the purpose of producing images is becoming increasingly well known. This is particularly true in the medical and diagnostic arts where magnetic resonance imaging (MRI) systems have become a commonplace and often indispensable tool for the diagnosis of many conditions.

A typical MRI system, of the type used for medical diagnosis, includes four major components. The first of these components is a large fixed-pole magnet. The fixed-pole magnet is formed to establish a channel dimensioned to receive a patient's entire body. The fixed-pole magnet may be of the permanent or electromagnetic type. Increasingly, however, the fixed-pole magnet is constructed as a cryogenic superconducting magnet, due largely to the ability of such magnets to provide a strong, stable magnetic field without the great mass associated with permanent magnets or the high power consumption associated with electromagnets. Functionally, the fixed-pole magnet operates to establish a strong and highly homogeneous static magnetic field within the channel established by the magnet.

The second major component of a typical MRI system is a system of gradient and radio frequency coils. Functionally, these coils, which may be implemented using a wide range of differing designs and types, operate to direct weak magnetic fields into the channel established by the fixed-pole magnet. The coils are positioned so that the weak magnetic fields are directed along a three-axis coordinate system. Additionally, the coils include a control mechanism that allows the fields to be alternately enabled and disabled.

The third and fourth major components found in a typical MRI system are a radio sensing system and a computer imaging system. The radio sensing system is, in simple terms, an antenna, which operates to collect radio frequency energy emitted by atomic nuclei under conditions created by the combined magnetic fields present in the MRI system. The computer imaging system is connected to the radio sensing system and performs various convolutions on the signals gathered by the radio sensing system to produce visual images corresponding to those signals.

In the operation of a typical MRI system, a patient, or other object, is positioned in the channel established by the fixed-pole magnet. Once positioned, the static magnetic field produced by the fixed-pole magnet interacts with some of the atomic nuclei contained within the tissues of the patient. As a result of the interaction caused by the static magnetic field, these atomic nuclei will tend to become aligned with the static magnetic field. The result is that the static magnetic field will tend to impart a net magnetic orientation to the atomic nuclei contained within the tissues of the patient.

While the patient is positioned within the channel established by the fixed-pole magnet, the gradient and radio frequency coils are selectively enabled and disabled to establish a series of weak magnetic fields within the channel. Not unexpectedly, the atomic nuclei which have become aligned by the static magnetic field become realigned under the influence of the weak magnetic fields. The alignment produced by the weak magnetic fields is, however, temporary and each atomic nuclei regains its normal orientation when the weak magnetic fields are disabled.

The return of the atomic nuclei to their normal orientation is known as spin relaxation and is accompanied by a release of radio energy from the atomic nuclei. The energy emitted during spin relaxation is known as a spin echo and is received by the radio sensing system providing the sensing system with information about the location of each nuclei that undergoes the process of relaxation. By alternately enabling and disabling weak magnetic fields, the location of the atomic nuclei may be accurately recorded by the radio sensing system. The information gathered by the radio sensing system is transmitted to the imaging computer system where the location of each atomic nuclei may be plotted in a three-dimensional image of the patient's tissues.

The basic MRI technology, as described above, has proven to be a highly effective tool for medical and other diagnostic purposes. In fact, the effectiveness of this technology has lead to the widespread use of MRI systems, making such systems somewhat commonplace in the medical field. Not unexpectedly, the success of MRI technology has also spurred numerous efforts to produce improvements to the basic MRI system. Many of these efforts have been directed at the production of MRI systems which produce high resolution images of large anatomical objects viewed.

One way of enhancing MRI image quality is the use of magnetic systems which produce highly uniform, or homogeneous, magnetic fields within the channel. Unfortunately, it has long been recognized that no magnetic field is perfectly homogeneous. Instead, the strength of the field produced by a magnet, or flux density $B_0$, varies as a function of position in relation to the magnet's two poles. For example, if it is assumed that an axis Z passes through the north and south poles of a magnet, it will be the case that the flux density $B_z$ will reach a maximum value at locations on the axis Z which are immediately adjacent to the north or south poles. At the same time, $B_z$ will reach a minimum value at the point on the Z axis which is midway between the north and south poles. Mathematically, saying that $B_z$ reaches a minimum value at the point midway between the north and south poles is equivalent to saying that the first derivative of $B_z$ or $$\frac{dB_z}{dZ}$$

is zero at that point.

MRI manufactures have long appreciated that more extensive homogeneous magnetic fields may be produced by using larger magnets to increase the volume, or sweet spot, around the midpoint where $$\frac{dB_z}{dZ}$$

is zero, or nearly zero. At the same time, it has been recognized that even this objective also achieved by fields whose higher order derivatives of $B_z$, such as $$\frac{d^2B_z}{dZ^2} \text{ and } \frac{d^3B_z}{dZ^3}$$

are also zero. For example, U.S. Pat. No. 5,400,786 which issued to Allis for an invention entitled "MRI Magnets" is directed at a specific arrangement of magnets and shims intended to produce a substantially homogeneous magnetic field. In any event, with an increase in the relative size of the homogenous field region, a larger anatomical volume of tissue may be imaged.

The present invention recognizes that large volumes of tissue do not always need to be imaged. Indeed, MRI systems may be constructed which are usefully directed at the production of relatively small images such as a small sample of the skin tissue. MRI systems of this type may be constructed by utilizing a static magnetic field which exhibits less extensive, homogeneity having a sweet spot where $$\frac{dB_z}{dZ}$$

is zero but wherein higher order derivatives, such as $$\frac{d^2B_z}{dZ^2} \text{ and } \frac{d^3B_z}{dZ^3}$$

are non-zero. Potentially, low-cost MRI systems of this type might be directed at imaging human skin, both for diagnostic as well as educational purposes.

In light of the above, it is an object of the present invention to provide an MRI system which is useful for the in vivo imaging of very small superficial volumes of tissue, such as skin samples. Another object of the present invention is to provide an MRI system whose imaging volume is small in comparison to the overall size of the system. Yet another object of the present invention is to provide an MRI system which is relatively simple to manufacture, easy to use, and comparatively cost effective.

SUMMARY OF THE PREFERRED EMBODIMENTS

The present invention is an MRI system for imaging small superficial volumes of tissue, such as skin samples. Structurally, the present invention includes a permanent magnet which is preferably of the rare-earth type and which is formed to establish a channel or gap between the poles of the magnet that is around ten to twenty centimeters wide. As intended for the present invention, the width of the channel is much larger than the imaging volumes. For example, the imaging volume can be around ten millimeters in diameter. In light of the relative dimensions given here, it is to be appreciated that a small volume image can be obtained from the surface of a large anatomical object such as a human forearm. Within the channel, the permanent magnet establishes a static magnetic field which has a magnitude of approximately two-tenths of one Tesla (0.2 T).

Importantly, as intended for the present invention, the homogeneous region of the magnetic field generated by the permanent magnet is limited in its extent. Specifically, for purposes of description, it may be assumed that an axis Z passes through the north and south poles of the permanent magnet. The sweet spot, which is centered around a point on the Z axis that is midway between the north and south poles, is characterized by a flux density $B_z$ having a first derivative $$\frac{dB_z}{dZ}$$

which is zero. The second order derivative of $B_z$, $$\frac{d^2B_z}{dZ^2},$$

and higher order derivatives however, need not and most likely are not zero.

In addition to the permanent magnet, the system of the present invention includes a probe assembly which is formed with a tip. The probe is attached to the permanent magnet with the tip of the probe positioned to be adjacent to the sweet spot within the channel and midway between the magnet pole faces where $$\frac{dB_z}{dZ}$$

is zero. A set of coils is mounted on the tip of the probe to simultaneously emit gradient and radio frequency signals and receive energy emitted by atomic nuclei during spin relaxation. Optionally, the tip of the probe may be equipped with an attachment system allowing the probe to be fixed against the object to be imaged.

The final component of the present invention is an imaging and control computer which is connected, via a bidirectional link, to the probe assembly. In general terms, it may be appreciated that the imaging and control computer performs the dual task of controlling the gradient radio frequency signal generated by the coil mounted at the tip of the probe assembly as well as analyzing the data received from the same coil. To perform these tasks, the imaging control computer selectively enables and disables outputs as well as selecting the particular frequency characteristics of the gradient and radio frequency signals. At the same time, the imaging and control computer receives and digitizes the radio signals gathered by the coil and assembles the resulting digitized data into a representation of the object being imaged. In a preferred embodiment, only one gradient field is used in order to encode and resolve the tissue content in a single direction, perpendicular to the superficial surface. In this embodiment, a one dimensional image of the skin surface is obtained.

In operation of the present invention, a small object, such as a human hand, is placed in the channel or gap established between the pole forces of the permanent magnet. Specifically, the area of the object (e.g. skin on the hand) to be analyzed is placed against the tip of the probe. Recall, this tip is positioned midway between the pole forces of the magnet where $$\frac{dB_z}{dZ} = 0.$$

Once so placed, the static magnetic field emitted by the permanent magnet orients some of the atomic nuclei within the object, giving the object a net magnetic alignment which follows the static magnetic field. The coils are then activated to direct gradient and radio frequency signals into the object. The gradient and radio frequency signals realign the atomic nuclei previously oriented by the static magnetic field. At the end of a predetermined orientation period, the gradient and radio frequency signals are disabled and the atomic nuclei realign with the static magnetic field. The spin echoes emitted by the realigning atomic nuclei are received by the coil mounted at the tip of the probe assembly. The spin echoes are then processed by the imaging and control computer. The orientation and relaxation cycle is then repeated as the imaging and control computer selectively enables and disables the gradient radio frequency coils. With each additional cycle, the imaging and control computer processes the resulting spin echoes and constructs a visual representation of the object being viewed. In the preferred embodiment, the visual representation provides a depth profile of the skin.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
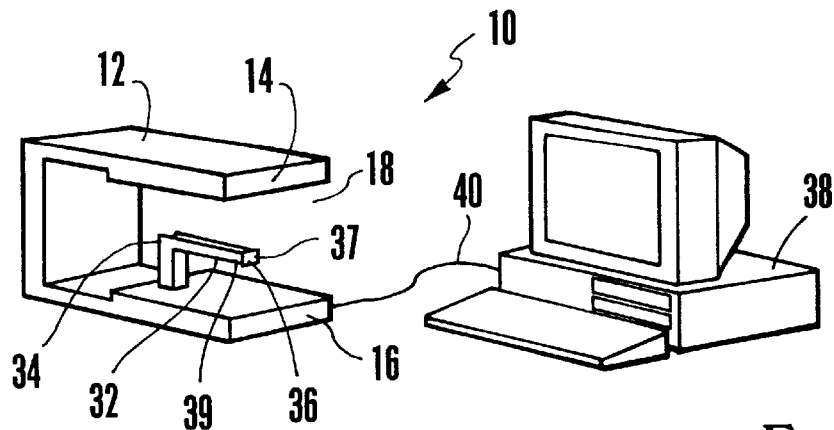
FIG. 1 is a pictorial view of the MRI system of the present invention.

The present invention is an MRI system for imaging small superficial volumes, such as skin samples. The structural details of the present invention may be better appreciated by initial reference to FIG. 1 where the system of the present invention is shown and generally designated 10. In more detail, it may be seen that the system 10 of the present invention includes a permanent magnet 12 having a generalized U-shape. The permanent magnet 12 is formed from a rare-earth or ceramic material and has a north pole 14 and south pole 16. As can be appreciated by cross referencing FIGS. 1 and 2, the north pole 14 and the south pole 16 of permanent magnet 12 can be formed as substantially square plates. Between the north pole 14 and south pole 16, the U-shape of permanent magnet 12 establishes a channel 18, preferably dimensioned approximately 10 cm or 20 cm in width in order to receive an object to be imaged, such as a human hand (not shown). In general, it may be appreciated that the U-shape shown for the permanent magnet 12 is intended to be exemplary in nature and that other shapes may be equally practical. In particular, it may be appreciated that any shape that establishes the required channel 18 between the north and south poles of a magnet may be appropriate. Further, for purposes of the present invention it is to be appreciated that in place of the permanent magnet 12, any device known in the pertinent art may be used to generate a static magnetic field 20. For instance, a superconductor magnet of a type well known in the art may be used.

Figure 2:
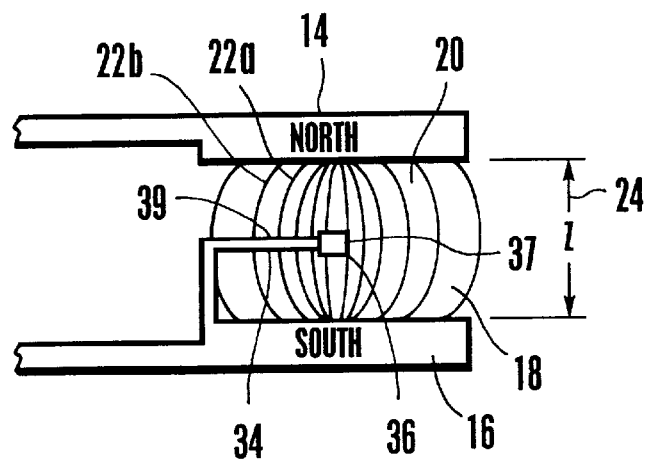
FIG. 2 is a schematic representation of the permanent magnet of the present invention.

Turning now to FIG. 2, it may be seen that the permanent magnet 12 establishes a static magnetic field 20 in the channel 18 between the north pole 14 and south pole 16. Preferably, the magnetic field 20 has a field strength of approximately two-tenths of one Tesla (0.2 T). The magnetic field 20 is characterized diagramatically by flux lines of which flux lines 22a and 22b are representative. Each flux line 22 has a slightly curving, arc shape which generally follows an axis Z designated 24. As indicated by the curving shape of the flux lines 22, the magnetic field 20 has a homogeneous field region whose volume is small in comparison with the overall dimension of the magnet and channel. More specifically, it may be assumed that the magnetic field 20 is characterized by a flux density which is represented symbolically as $B_0$. The component of the magnetic flux density which is aligned with the Z-axis 24 is referred to as $B_z$. In FIG. 2, the flux density $B_z$ may be thought of as the number of flux lines 22 which traverse a given area. A result of the curvature of the flux lines 22, is that the flux density $B_z$ varies depending on the area within channel 18. This is, of course, apparent by comparison of areas which are located near either the north pole 14 or south pole 16 with similarly sized areas distanced from the north pole 14 and south pole 16.

Figure 3:
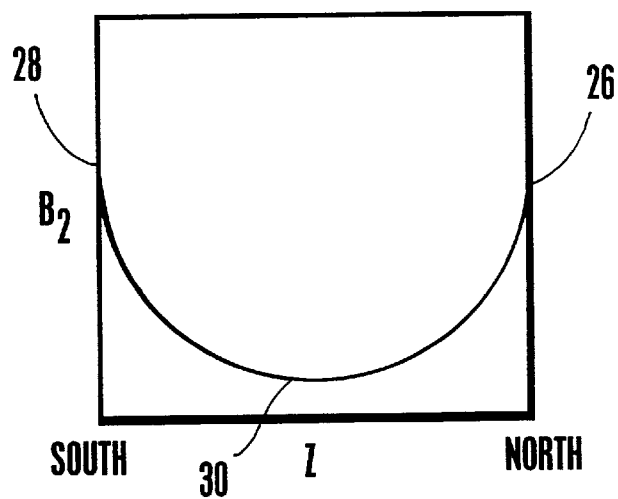
FIG. 3 is a graphical representation of the magnetic field density produced by the permanent magnet of the present invention.

The relationship between the flux density $B_z$ and location within the channel 18 may be better appreciated by reference to FIG. 3 where flux density $B_z$ is shown as a function of position along Z-axis 24. As may be seen from FIG. 3, flux density is greatest at points 26 and 28 which correspond to locations adjacent to the north pole 14 and south pole 16 respectively. It may be seen that flux density $B_z$ reaches a minimal value at point 30 which corresponds to an area which is equidistant from north pole 14 and south pole 16. Additionally, it may be seen that point 30 is a point of inflection and satisfies the equation $$\frac{dB_z}{dZ} = 0.$$

For the purposes of the present invention, a small volume surrounding point 30, which includes the point where $$\frac{dB_z}{dZ}$$

is substantially zero, is defined as the region within channel 18 where the magnetic field is homogeneous. Importantly, while the definition of partial homogeneity requires that $$\frac{dB_z}{dZ}$$

be zero, the present invention accepts the fact that higher order derivatives may have absolute values and be non-zero. In particular, it is accepted that $$\frac{d^2B_z}{dZ^2}$$

is not zero. As a result, the imaging volume surrounding point 30 is small, measuring approximately one centimeter, but more probably, 5 millimeters in diameter.

Referring again to FIG. 1, it may be seen that the present invention also includes a probe assembly 32. The probe assembly 32 is shaped to have a body 34 and a tip 36. The body 34 is attached to the permanent magnet 12 to position the tip within the channel 18 adjacent to the imaging volume of the permanent magnet 12 Optionally, the tip 36 of the probe 32 may be equipped with an attachment system 37 allowing the probe to fixed against the object to be imaged. An attachment system 37 of this type may be implemented as a suction cup (not shown) or an adhesive as shown in FIGS. 1 and 2.

Gradient and radio frequency coils 39 are mounted within the tip of the probe assembly 32. For the purposes of the present invention, it has been found to be particularly efficient to implement both the gradient and radio frequency coils 39 using a surface coil as is well known in the pertinent art.

Continuing with FIG. 1, it may be seen that the system 10 of the present invention also includes an imaging and control computer 38. The imaging and control computer 38 is connected via a bi-directional link 40 to the probe assembly 32. The bi-directional link 40 allows the imaging and control computer 38 to receive signals from the radio sensing antenna included in the tip 36 of the probe assembly 32. At the same time, the bi-directional link 40 allows the imaging and control computer 38 to send signals to be emitted from the gradient radio frequency coil included in the tip 36 of the probe assembly 32.

OPERATION

In operation of the system 10 of present invention, a small object, such as a human hand (not shown), is placed in the channel 18 formed in the permanent magnet 12. The placement of the object to be imaged places the object, and in particular the subsection of the object that will be imaged, at the homogeneous field of the magnetic field 20. Exposure to the static magnetic field orients some of the atomic nuclei within the object, giving the object a net magnetic alignment which follows the Z-axis 24.

The imaging and control computer 38 then activates the gradient and radio frequency coils included in the tip 36 of the probe assembly 32. The gradient and radio frequency signals emitted by the probe realign the atomic nuclei previously oriented by the static magnetic field 20 to follow the Z-axis 24. At the end of a predetermined orientation period, the imaging and control computer 38 disable the gradient and radio frequency coils included in the tip 36 of the probe assembly 32. Disabling the gradient radio frequency coil allows the atomic nuclei to realign with the Z-axis 24. In the process, each atomic nuclei emits an encoded radio signal, or spin echo, which is then received by the radio sensing antenna mounted at the tip 36 of the probe assembly 32.

The spin echoes are then digitized using a fast fourier transformation and assembled by the imaging and control computer 38 into a visual representation of the object being imaged. The steps of activating and disabling the gradient and radio frequency coils included in the tip 36 of the probe assembly 32 may be repeated to further define the visual representation created by the system 10.

While the particular MRI system for imaging small superficial volumes as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A magnetic resonance system for imaging a skin sample which comprises:
    a magnet having a North pole face and a South pole face, said North pole face being separated from said South pole face in a Z direction to form a channel therebetween, said magnet generating a static magnetic field having a field strength in said Z direction of $B_z$, and said magnet creating an imaging volume in said channel midway between said North pole face and said South pole face wherein $$\frac{dB_z}{dZ}$$

is equal to zero and $$\frac{d^2B_z}{dZ^2}$$

has an absolute value greater than zero;
    probe assembly having a tip, said probe assembly being positioned on said magnet with said tip adjacent said imaging volume;
    a gradient and radio frequency coil assembly mounted on said tip of said probe assembly to generate spin echos from the skin sample when the skin sample is positioned adjacent said tip;
    an antenna mounted on said probe assembly for recording said spin echos; and
    an imaging computer electronically connected with said antenna to convert said spin echos into an image of the skin sample.

2. A system as recited in claim 1 wherein said tip of said probe assembly is fixedly held in said static magnetic field and wherein said North pole face is separated from said South pole face by a distance in a range of approximately ten centimeters to approximately twenty centimeters.

3. A system as recited in claim 1 wherein said magnet is a permanent magnet.

4. A system as recited in claim 3 wherein said permanent magnet is a rare earth magnet.

5. A system as recited in claim 3 wherein said permanent magnet is a ceramic magnet.

6. A system as recited in claim 3 wherein said permanent magnet is formed as square plates.

7. A system as recited in claim 1 wherein said imaging volume is substantially spherical and has a diameter of less than one centimeter.

8. A system as recited in claim 1 wherein said field strength is approximately two-tenths of one Tesla (0.2 T).

9. A system as recited in claim 1 further comprising means for stationarily holding said skin sample against said tip of said probe assembly.

10. A system as recited in claim 9 wherein said holding means is a suction device.

11. A system as recited in claim 9 wherein said holding means is an adhesive.

12. A method for magnetic resonance imaging of a skin sample which comprises the steps of:
    providing a system having means for creating a static magnetic field, said system being formed with a channel dimensioned to provide access for placement of a human anatomy containing said skin sample within said static magnetic field, said system further including a probe assembly having a tip with a gradient and radio frequency coil mounted at said tip of said probe assembly and a radio frequency antenna mounted on said probe assembly, and means for positioning said tip of said probe assembly adjacent a point in said static magnetic field where $$\frac{dB_z}{dZ} = 0 \text{ and } \frac{d^2B_z}{dZ^2}$$

has an absolute value greater than zero;
    inserting said anatomy containing said skin sample through said channel to position said skin sample against said tip of said probe assembly;

activating said gradient and radio frequency coil to generate spin echos from the skin sample when the skin sample is positioned adjacent said tip;

receiving said spin echos with said antenna; and converting said spin echos into an image of the skin sample.

13. A magnetic resonance system for imaging skin which comprises:

static magnetic means for creating a static magnetic field, said means being formed with a channel being dimensioned to provide access for placement of an object containing said skin within said static magnetic field adjacent a point in said static magnetic field where $$\frac{dBz}{dZ} = 0 \text{ and } \frac{d^2B_z}{dZ^2}$$

has an absolute value greater than zero;

variable magnetic means for creating a variable magnetic field in said channel;

control means for said variable magnetic means to cause atomic nuclei within said skin to alternate between a tilted state and a relaxed state;

antenna means for gathering echoes produced by said nuclei as said nuclei alternate between said tilted state and said relaxed state; and processing means for transforming said gathered echoes to produce an image of said skin.

14. A system as recited in claim 13 wherein said static magnetic means includes a permanent magnet having two pole faces.

15. A system as recited in claim 14 wherein said permanent magnet is a rare earth magnet.

16. A system as recited in claim 14 wherein said permanent magnet is a ceramic magnet.

17. A system as recited in claim 14 wherein said poles faces are formed as square plates.

18. A system as recited in claim 13 wherein said static magnetic means creates a static magnetic field having a field strength of approximately two-tenths of one Tesla (0.2 T).

19. A system as recited in claim 13 wherein said variable magnetic means includes a radio frequency coil.

20. A system as recited in claim 19 wherein said antenna means includes a radio frequency antenna.

21. A system as recited in claim 20 further comprising a probe having a tip and wherein said radio frequency coil and said radio frequency antenna are mounted to said tip to said probe.

* * * * *

UNITED STATES PATENT AND TRADEMARK OFFICE
CERTIFICATE OF CORRECTION

PATENT NO. : 5,855,555
DATED : January 5, 1999
INVENTOR(S) : Christopher W. Crowley It is certified that error appears in the above-identified patent and that said Letters Patent is hereby corrected as shown below:

On the title page item 75
Inventor's name
DELETE
[Crowely]
INSERT
--Crowley--

Column 6, Line 60
INSERT
-- . -- following magnet 12 and before the word Optionally Column 6, Line 62
INSERT
--be-- following the words probe to and before the word fixed Column 7, Line 18
INSERT
--the-- following system 10 of and before the word present Column 9, Line 4 and Line 5
DELETE
[echos]
INSERT
--echoes--

UNITED STATES PATENT AND TRADEMARK OFFICE
CERTIFICATE OF CORRECTION

PATENT NO. : 5,855,555
DATED : January 5, 1999
INVENTOR(S) : Christopher W. Crowley It is certified that error appears in the above-identified patent and that said Letters Patent is hereby corrected as shown below:

Column 10, Line 12

Delete "poles insert--pole--

Signed and Sealed this

Twenty-fifth Day of May, 1999

Attest:

Q. TODD DICKINSON

*Attesting Officer*      *Acting Commissioner of Patents and Trademarks*